United States Patent [19]

Zhu

[11] Patent Number: 5,454,860
[45] Date of Patent: Oct. 3, 1995

[54] SYSTEM FOR GENERATING AND PROVIDING A GASEOUS PHASE SAMPLE AT RELATIVELY SEQUENTIALLY CONSTANT PRESSURE AND FLOW RATE

[75] Inventor: Jianzhong Zhu, Omaha, Nebr.

[73] Assignee: Cetac Technologies Inc., Omaha, Nebr.

[21] Appl. No.: 177,219

[22] Filed: Jan. 4, 1994

[51] Int. Cl.[6] .................................................. B01D 19/00
[52] U.S. Cl. ............................. 96/202; 55/462; 95/262; 96/204; 96/220
[58] Field of Search .............................. 96/189, 204, 206, 96/220, 202; 95/262, 272; 55/462, 465

[56] References Cited

U.S. PATENT DOCUMENTS

| | | | |
|---|---|---|---|
| 1,127,722 | 2/1915 | Beckley | 96/220 X |
| 1,255,018 | 1/1918 | Jones | 96/204 X |
| 2,336,430 | 12/1943 | Wery | 96/204 |
| 2,489,893 | 11/1949 | Johnson | 73/863.21 |
| 2,884,366 | 4/1959 | Anderson et al. | 204/408 |
| 3,116,999 | 1/1964 | Armbruster | 75/511 |
| 3,477,279 | 11/1969 | Perlahy | 73/863.21 X |
| 3,819,331 | 6/1974 | Weber | 96/204 X |
| 3,926,594 | 12/1975 | Seib et al. | 96/220 |
| 4,002,432 | 1/1977 | Brice et al. | 96/204 X |
| 4,504,396 | 3/1985 | Vasdi et al. | 210/800 |
| 4,559,808 | 12/1985 | Sturman | 55/462 X |
| 4,668,252 | 5/1987 | Gerdau | 55/465 X |
| 4,744,958 | 5/1988 | Pircon | 55/465 X |
| 5,021,070 | 6/1991 | Birbara et al. | 96/204 X |
| 5,114,445 | 5/1992 | Burton et al. | 55/465 X |
| 5,162,651 | 11/1992 | Nato | 250/288 |

*Primary Examiner*—Richard L. Chiesa
*Attorney, Agent, or Firm*—James D. Welch

[57] ABSTRACT

A system and method of use for providing nearly one-hundred (100%) percent of volatile component(s) present in a liquid solution as a gaseous phase volatile component(s) sample to a sample analysis system, at relatively sequentially constant buffered pressure and flow rate, is disclosed. The present invention also provides for quick, immediate and active removal of a remaining liquid solution mixture entered thereto to reduce carry-over contamination. The present invention is particularly well suited for use with flame and plasma based sample analysis systems and its use serves to greatly increase achievable stability of their operation, and sensitivity to volatile component(s) such as, As, Se, Sb, Sn, Hg, B and Te.

7 Claims, 1 Drawing Sheet

SYSTEM FOR GENERATING AND PROVIDING A GASEOUS PHASE SAMPLE AT RELATIVELY SEQUENTIALLY CONSTANT PRESSURE AND FLOW RATE

TECHNICAL FIELD

The present invention relates to analysis of gaseous phase volatile component(s) samples. More particularly the present invention is a system, and method of use, for accepting a volatile component(s) containing liquid solution mixture and providing volatile component(s) therein in a generated gaseous phase at a relatively sequentially constant buffered flow rate and elevated pressure, while simultaneously providing for quick, immediate and active removal of remaining liquid solution mixture to prevent subsequent procedure contamination.

BACKGROUND

Chemical reaction mediated generation of gaseous phase volatile component(s) originally present in a containing liquid solution is a widely used technique for providing gaseous phase volatile component(s) for introduction to sample analysis systems such as those utilizing atomic spectrometry, (eg. flame atomic absorbtion spectrometry, flame atomic emission spectrometry, inductively coupled plasma atomic emission spectrometry and inductively coupled plasma mass spectrometry). Said technique generates nearly one-hundred (100%) percent of the volatile component(s) present in a containing liquid solution into a gaseous phase. This compares to about two (2%) percent achievable with pneumatic nebulizers and twenty (20%) percent achievable with ultrasonic nebulizers. It will then be appreciated that volatile component(s) sample sensitivity achievable by practice of the identified technique is high.

The identified technique is especially well suited to use in the analysis of As, Se, Sb, Bi, Sn, Hg, B and Te, for instance.

Continuing, the identified technique typically provides that a volatile component(s) containing liquid solution should be mixed with an agent, typically HCl, to provide an acidified first solution mixture, which acidified first solution mixture is then further mixed with a second agent, such as $NaBH_4$ or $SnCl_2$, to provide a second solution mixture. Said second solution mixture is then typically caused to flow through a length of enclosed volume flow path, (typically coiled tubing), so that chemical reactions between volatile component(s) in the mixed liquid solution and the added agents can occur. The resulting chemically reacting second solution mixture is then typically caused to impinge upon a surface area providing means to provide chemically reacting second solution mixture in a sheet form, from which sheet of chemically reacting second solution mixture, gaseous phase volatile component(s) containing sample is released as quantized "bubbles".

While systems which utilize the disclosed technique are commonly used, certain problems typically associated with such known systems are:

1. Gaseous phase generation of volatile component(s) from a liquid solution mixture fluctuates with time. This, as alluded to, is because the generation of volatile component(s) in a gaseous phase is mediated by chemical reaction quantized "bubble" formation in the identified second solution mixture. Said generated "bubbles" are sequentially released in varying quantities per unit time. This directly leads to variations in gaseous phase volatile component(s) sample flow rate into a receiving sample analysis system. It is noted that such fluctuations can, for instance, cause ICP instability and accompanying negative analysis results. In the extreme an ICP Plasma can even be extinguished by such fluctuations.

2. Typical known systems which utilize chemical reactions to provide gaseous phase volatile component(s) sample utilize a passive gravity driven "U" shaped drain for removing liquid solution mixture which remains after the gaseous phase volatile component(s) sample has been generated therefrom. Said liquid solution mixture is typically not immediately removed from said system and can continue to provide gaseous phase volatile component(s) sample which can find its way into the sample analysis system. This can cause typical known systems to be demonstrate a "memory" effect. That is for instance, if all remaining liquid solution mixture is not quickly and immediately removed after performing one procedure, and before beginning another, gaseous phase volatile component(s) sample from the earlier procedure can continue to be provided to the gaseous phase volatile component(s) sample produced during a subsequent procedure.

A search of Patents has provided little in the way of relevant art. A Patent to Sturman is perhaps the best reference discovered and describes a gas/liquid separator comprising a separation chamber and first solution and second solution inlets for entering gas thereinto. In use a volatile component containing liquid solution mixture is caused to flow into the separator chamber and impinge upon an enlarged portion of an upwardly extending tube therein, the outer surface of which enlarged portion of said upwardly extending tube serves to mediate gaseous phase volatile sample component release from said impinging liquid solution mixture. Entered gas flows aid both sample solution entry, and gaseous phase volatile sample flow through the gas/liquid separator chamber. There is no provision in the Sturman system, however, which would allow a controlled increased quantized bubble formation pressure buffering effect to be achieved in the gas/liquid separator chamber. That is, said gas/liquid separator chamber is not capable of supporting an elevated internal pressure. Nor is there any provision in the Sturman system for quick and immediate active removal of remaining liquid solution mixture from the system. Other Patents identified, but not considered particularly relevant, are: U.S. Pat. Nos. 4,504,396 to Yardi et al., 1,255,018 to Jones, 4,002,432 to Brice et al., 3,819,331 to Weber, 3,477,279 to Perlaky, 3,116,999 to Armbruster, 2,884,366 to Anderson et al., 2,336,430 to Wery, 2,489,893 to Johnson and 5,162,651 to Kato.

A need is thus identified, which the present invention meets in the form of a system and method of use which serves to overcome the identified problems.

DISCLOSURE OF THE INVENTION

The present invention is comprised of an elevated internal pressure supporting gas/liquid separator chamber which includes a surface area providing means. Said elevated internal pressure supporting gas/liquid separator chamber also comprises a liquid sample entry means which is oriented so as to, during use, allow a volatile component(s) containing liquid solution mixture to be impinged upon said surface area providing means, a drain outlet for attachment to an actively controlled sealed pump, a gaseous phase volatile components(s) sample outlet port and a carrier gas inlet port. The gaseous phase volatile component(s) sample outlet port typically includes an elevated pressure maintaining relatively small internal diameter coiled tube, which relatively small internal diameter coiled tube provides access to a sample analysis system.

During use a volatile component(s) containing sample solution is typically caused, in elements external to the elevated internal pressure supporting gas/liquid separator chamber, to be mixed with a first agent to provide a resulting acidified first solution mixture. Said acidified first solution mixture is then caused to be mixed with a second agent to provide a second solution mixture, which second solution mixture is caused to flow through a length of enclosed volume flow path to provide time for chemical reactions to occur in said second solution mixture before being caused to enter said liquid sample entry means in the elevated pressure supporting gas/liquid separator chamber and being impinged upon the surface area providing means. As said "chemically reacting" second solution mixture flows over the surface area providing means, quantized gaseous phase "bubbles" of volatile component(s) are released into said elevated pressure supporting gas/liquid separator chamber wherein they combine into a relatively homogeneous volume of gas and are caused to flow out of the gaseous phase volatile component sample outlet port toward a sample analysis system. Said flow is typically aided by a carrier gas which is entered into said carrier gas inlet port. Typically, but not necessarily, said carrier gas inlet port is oriented so as to provide gaseous phase sample flow enhancing tangentially oriented carrier gas flow inside said elevated internal pressure supporting gas/liquid separator chamber. That is, said carrier gas typically is entered so as to flow perpendicularly to the surface of the surface area providing means in a spiral-like motion toward the gaseous phase volatile component(s) sample outlet port. During the above described processes, a sealed pump which is attached to the drain outlet serves to actively, quickly and immediately remove remaining liquid second solution mixture which drains from the surface of the surface area providing means, in a controlled manner.

It emphasised that the present invention system allows an elevated internal pressure to be maintained inside the elevated internal pressure supporting gas/liquid separator chamber by control of the volatile component(s) containing second solution mixture entry flow rate thereinto, the carrier gas flow rate thereinto and the actively driven sealed pump, remaining liquid second solution mixture removal flow rate therefrom. Maintenance of said elevated internal pressure serves to buffer the effect of the sequentially variable formation rate of quantized volatile component(s) gaseous phase bubbles during use, as observed at the gaseous phase volatile component(s) sample outlet port and at the input to a directly, or indirectly, attached sample analysis system. It is also emphasised that quick, immediate and active sealed pump controlled removal of remaining liquid second solution mixture which flows from the surface of the surface area providing means, assures that carry-over problems based in continued release of bubbles of volatile component(s) containing gaseous phase sample during subsequent analysis procedures will not be possible.

It should then be appreciated that the present invention allows overcoming problems associated with sequentially variable rates of release of quantized bubbles of gaseous phase volatile component(s) sample from a chemically reacting liquid solution mixture impinged upon a surface area providing means in an elevated internal pressure supporting gas/liquid separator chamber, and carry-over problems associated with allowing remaining liquid second solution mixture to remain therein.

The present invention will be better understood by reference to the Detailed Description Section of this Disclosure in conjunction with the accompanying Drawings.

SUMMARY OF THE INVENTION

Chemical reaction generation of gaseous phase volatile component(s) originally present in a containing liquid solution which is mixed with various agents to provide a liquid solution mixture, is a widely used technique for providing gaseous phase volatile component(s) sample for introduction to sample analysis systems.

Problems which present in use of known systems for practicing the technique are based in a chemical reaction mediated sequentially variable gaseous phase volatile component(s) "bubble" generation rate, and in a failure to quickly remove remaining volatile component(s) containing liquid solution mixture from a gas/liquid separator after a majority of said volatile component(s) have been generated into a gaseous phase, thereby leading to carry-over problems.

The present invention provides a system and method of use which effectively overcomes the identified problems by providing an elevated internal pressure supporting gas/liquid separator system which is capable of supporting an elevated internal volatile component(s) bubble generation rate buffering pressure, and which incorporates an active sealed pump for quickly, immediately and actively removing remaining liquid solution mixture.

It is therefore a purpose of the present invention to provide a system which is capable of providing a gaseous phase volatile component(s) sample at a relatively constant buffered output pressure and flow rate.

It is also a purpose of the present invention to provide a system which allows quick, immediate and active removal of remaining liquid solution mixture therefrom during use to prevent sample carry-over from one analysis procedure to a subsequent analysis procedure.

It is yet another purpose of the present invention to teach a method of use of the disclosed system.

DETAILED DESCRIPTION OF THE PREFERRED EMBODIMENT

Turning now to the drawings, it will be appreciated that the present invention is a system and method for providing a volatile component(s), (eg. As, Se, Sb, Sn, Pb, and Te), sample in a relatively sequentially constant buffered pressure and flow rate gaseous phase, suitable for introduction into, for instance, a flame or ICP sample analysis system.

Figure 1:
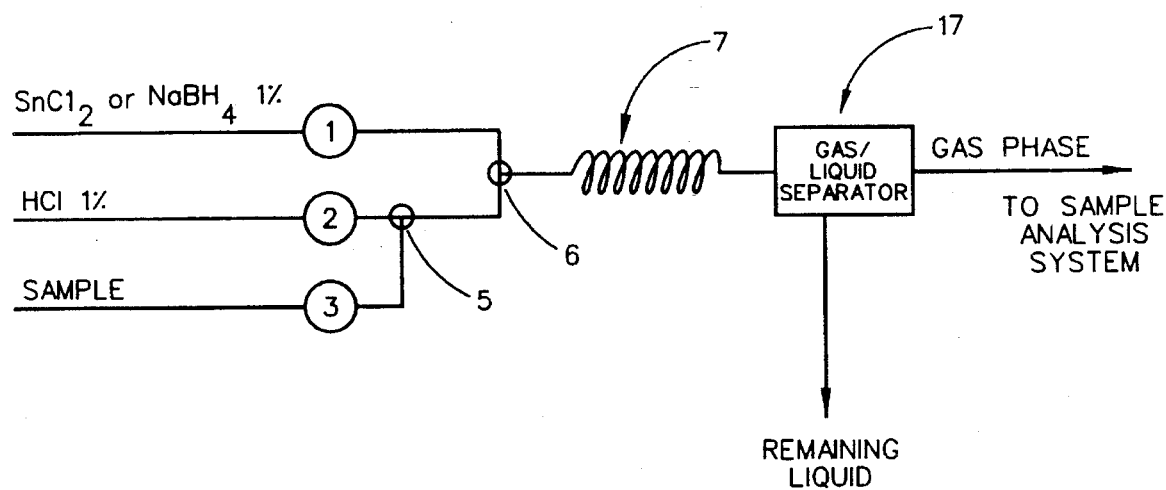
FIG. 1 shows a procedural flow diagram for the system of the present invention.

FIG. 1 shows a procedural flow diagram for the present invention. Pumps (2), (3), (typically peristaltic), serve to feed, typically, hydrochloric acid (HCl) and volatile component(s) containing liquid solution into mixing element (5) to provide an acidified first solution mixture. Next said acidified first solution mixture is caused to be mixed with, typically, sodium-borohydride (NaBH4) in mixing element (6) by pump (1) to form a second solution mixture. A length of enclosed volume flow path (7) directly follows and provides said second solution mixture flowing therethrough time to cause volatile sample component(s) present therein to begin reacting chemically with added agents. Said volatile component(s) containing chemically reacting second solution mixture is then caused to enter a liquid sample entry means (15), (see FIG. 2), in said elevated internal pressure supporting gas/liquid separator chamber (17) such that said second solution mixture is caused to be impinged upon a surface area providing means (13) therein, (again see FIG. 2). Gaseous phase volatile component(s) leave the second solution mixture in quantized bubble form and are transported into a sample analysis system, typically aided by a carrier gas flow entered at carrier gas inlet port (14). Remaining liquid second solution mixture which drains from surface area providing means (13) is quickly, immediately and actively removed via drain port (18) by attached sealed pump system (12). The important end result being that chemical reaction(s) cause volatile component(s) in the second solution mixture to become present in elevated pressure supporting gas/liquid separator chamber (17) in a relatively constant buffered pressure and flow rate gaseous phase suitable for entry into a sample analysis system such as those utilizing flames or ICP's.

It is to be noted that the system shown in flow diagram form in FIG. 1, can also be used to provide gaseous phase volatile component(s) sample such as Hg and B when other reagents, (eg. SnCl2 rather than NaBH4), are utilized to form the volatile component(s) containing liquid second solution mixture.

Figure 2:
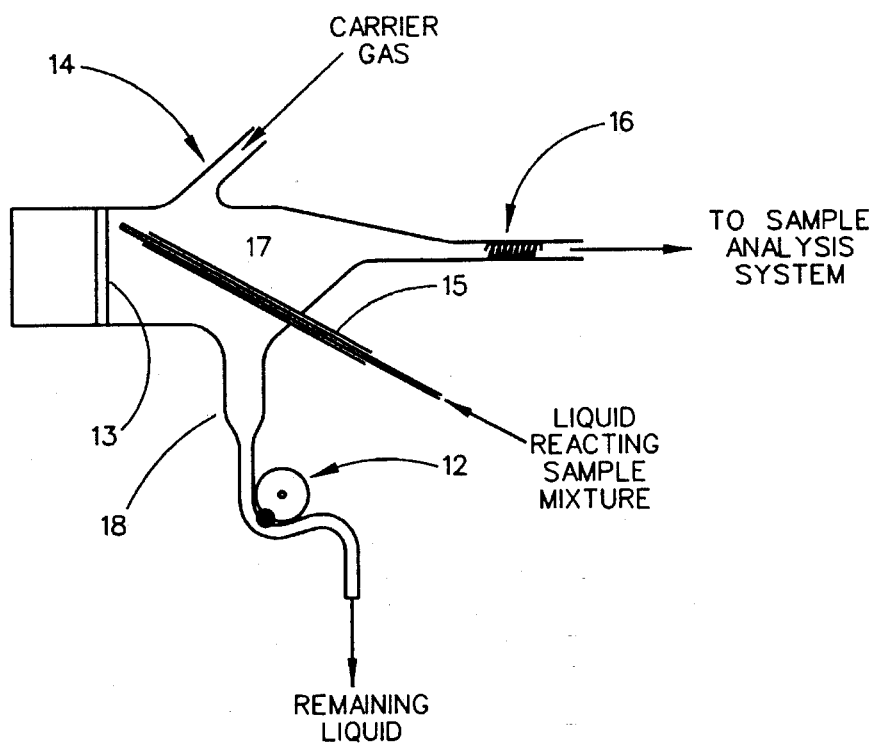
FIG. 2 shows a side elevational view of the elevated internal pressure supporting gas/liquid separator chamber of the present invention.

FIG. 2 makes it clear that the elevated internal pressure supporting gas/liquid separator chamber (17) identified in FIG. 1 is shown to be comprised of a drain outlet (18) to which is attached sealed pumping system (12) at its lower aspect, and with a gaseous phase volatile component(s) outlet port (16) at a position removed from a surface area providing means (13) therein. Said gaseous phase volatile component(s) outlet port (16) typically includes an elevated internal pressure maintaining length of small internal diameter tubing, shown as coiled in FIG. 2. Also shown as present is a carrier gas inlet port (14) and volatile component(s) containing second solution mixture liquid sample entry means (15).

It is to be appreciated that the elevated internal pressure supporting gas/liquid separator chamber (17) tapers as it merges into the gaseous phase volatile component(s) outlet port (16). This provides an aerodynamic shape which enhances the volatile component(s) containing gaseous sample transporting effect of tangentially directed carrier gas entered at carrier gas inlet port (14), which is typically present at an upper aspect of said elevated internal pressure supporting gas/liquid separator chamber. It should also be appreciated that the surface area providing means (13) is replaceable, oriented vertically and oriented with respect to the liquid sample entry means (15) so that during use entering volatile component(s) containing second solution mixture impinges thereon at an upper aspect thereof and flows under the influence of gravity down thereover toward drain outlet (18). The relatively large surface area provided by said surface area providing means (13) serves to increase gas/liquid separation during use.

During use volatile component(s) containing second solution mixture caused to exit the length of enclosed volume flow path (7) shown in FIG. 1 is caused to be impinged upon surface area providing means (13) in elevated internal pressure supporting gas/liquid separator chamber (17) via liquid sample entry means (15) by a pumping system, (not shown). Said volatile component(s) containing second solution mixture flows over surface area providing means (13) in a thin sheet, thereby providing a relatively large surface area from which gaseous phase volatile component(s) contained in volatile component(s) containing second solution mixture formed during chemical reactions can easily and efficiently escape. Remaining liquid solution in the second solution mixture flows into drain outlet (18) and is quickly, immediately and actively removed by sealed pumping system (12). Simultaneous with the above described procedure, a carrier gas is entered into the elevated internal pressure supporting gas/liquid separator chamber (17) via carrier gas inlet port (14). As mentioned, the carrier gas inlet port (14) is typically oriented so that said carrier gas follows an efficient tangentially oriented flow path, which aids the transport of gaseous phase volatile component(s) sample through gaseous phase volatile component(s) sample outlet port (16) and on to a sample analysis system such as a flame or ICP based system.

The present invention system provides benefits over known systems which operate on a similar principals as follows:

1. The elevated internal pressure supporting gas/liquid separator chamber (17) is capable of supporting an elevated internal pressure, hence gaseous phase volatile component(s) containing sample pressure and flow rate fluctuations which result from quantized, chemical reaction mediated, bubble production are buffered as monitored at the gaseous phase volatile component(s) outlet port (16). As a result sequential gaseous phase flow rate and elevated pressure are maintained at relatively constant buffered levels during use. The sealed pump system (12) and drain outlet (18) are interconnected in a manner such that entering volatile component(s) containing second solution mixture and produced volatile component(s) gaseous phase sample, as well as entered carrier gas, can serve to build an elevated pressure inside the elevated internal pressure supporting gas/liquid separator chamber (17) above that outside thereof.

2. It is specifically noted that the use of an entered tangentially oriented carrier gas flow at carrier gas inlet port (14), aids gaseous phase volatile component(s) sample exit from gaseous phase volatile component(s) outlet port (16) in a steady non-fluctuating manner.

3. It is also specifically noted that the surface area providing means (13) causes volatile component(s) containing second solution mixture impinged thereonto to form a relatively thin sheet as it flows thereover during use. This effects better quantized bubble gaseous phase volatile component(s) sample release from said second solution mixture liquid solution. This increases the efficiency and sensitivity achievable by the system.

4. Further, remaining liquid second solution mixture which enters the drain outlet (18) is removed quickly, immediately and actively by pumping system (12). This eliminates memory effect.

The present invention is then found in the system shown in FIGS. 1 and 2, and the method of its use.

Having hereby disclosed the subject matter of this invention, it should be obvious that many modifications, substitutions, and variations of the present invention are possible in light thereof. It is therefore to be understood that the invention may be practiced other than as specifically described, and should be limited in breadth and scope only by the

I claim:

1. A system for generating and providing a gaseous phase volatile component(s) sample to a sample analysis system at relatively sequentially constant buffered pressure and flow rate, via a gaseous phase volatile component(s) sample outlet port in an elevated internal pressure supporting gas/liquid separator chamber, which relatively constant buffered pressure is supported at an elevated level inside said elevated internal pressure supporting gas/liquid separator chamber, with respect to the surrounding exterior atmospheric pressure, and which gaseous phase volatile component(s) are originally present in a liquid solution mixture having entered by way of a liquid sample entry means, which system for generating and providing a gaseous phase volatile component(s) sample to a sample analysis system at relatively sequentially constant buffered pressure and flow rate comprises a drain outlet in a lower extent of said elevated internal pressure supporting gas/liquid separator chamber, to which drain outlet is attached a sealed pump system for use in quickly, immediately and actively removing remaining liquid solution mixture having entered said elevated internal pressure supporting gas/liquid separator chamber via said liquid sample entry means during use, after volatile gaseous phase component(s) have been generated therefrom in the form of quantized bubbles by a chemical reaction mediated process, and which system for generating and providing a gaseous phase volatile component(s) sample at relatively sequentially constant buffered pressure and flow rate further comprises an elevated internal pressure maintaining small inner diameter tube in the gaseous phase volatile component(s) sample outlet port, which liquid sample entry means, sealed pump and small inner diameter tube are incorporated positioned in said elevated internal pressure supporting gas/liquid separator chamber so that an elevated internal pressure is, during use, supported therein.

2. A system for generating and providing a gaseous phase volatile component(s) sample as in claim 1, which further comprises a surface area providing means, located inside said elevated internal pressure supporting gas/liquid separator chamber above said drain outlet and offset from said liquid sample entry, means, upon which surface area providing means volatile component(s) containing liquid solution mixture having entered via said liquid sample entry means, is caused to impinge during use, for the purpose of causing the spread of said impinging liquid solution mixture into a thin sheet of relatively large surface area so that volatile component(s) therein can be more easily released, by chemical reaction mediated generation, into a gaseous phase in the form of sequentially varying numbers of quantized bubbles, which sequentially varying numbers of quantized bubbles are caused to merge in the elevated internal pressure supporting gas/liquid separator chamber by elevated pressure therein, to provide said relatively sequentially constant buffered pressure and flow rate of gaseous phase volatile component(s) sample out of said gaseous phase volatile component(s) sample outlet port, said surface area providing means and said gaseous phase volatile component(s) outlet port being located at laterally opposed extents of said elevated internal pressure supporting gas/liquid separator chamber, above said drain outlet.

3. A system for providing gaseous phase volatile component(s) sample as in claim 2, which further comprises a carrier gas inlet port at the surface area providing means extent of elevated internal pressure supporting gas/liquid separator chamber, into which carrier gas is caused to flow during use to aid the flow of generated gaseous phase volatile component(s) sample through said gaseous phase volatile component(s) sample outlet port and into a sample analysis system attached thereto.

4. A system for providing gaseous phase volatile component(s) sample as in claim 3 in which said carrier gas having entered during use flows through said elevated internal pressure supporting gas/liquid separator chamber in a tangentially oriented spiral manner toward said gaseous phase volatile components sample outlet port, said elevated internal pressure supporting gas/liquid separator chamber being tapered in shape, narrowing toward said gaseous phase volatile component(s) sample outlet port.

5. A system for generating and providing a gaseous phase volatile component(s) sample to a sample analysis system at relatively sequentially constant buffered pressure and flow rate, via a gaseous phase volatile component(s) sample outlet port in an elevated internal pressure supporting gas/liquid separator chamber, which relatively constant buffered pressure is supported at an elevated level inside said elevated internal pressure supporting gas/liquid separator chamber, with respect to the surrounding exterior atmospheric pressure, and which volatile component(s) are originally present in a liquid solution mixture having entered by way of a liquid sample entry means, which generating and providing system includes a drain outlet in a lower extent of said elevated internal pressure supporting gas/liquid separator chamber, to which is attached a sealed pump system for use in quickly, immediately and actively removing remaining liquid solution mixture entered to said elevated internal pressure supporting gas/liquid separator chamber via said liquid sample entry means, after gaseous volatile component(s) have been generated therefrom in the form of quantized bubbles by a chemical reaction mediated process, and which system further comprises a surface area providing means inside said elevated internal pressure supporting gas/liquid separator chamber offset from said liquid sample entry means, upon which said entered volatile component(s) containing liquid solution mixture is caused to impinge during use, via said liquid sample entry means, for the purpose of causing the spread of said impinging volatile component(s) containing liquid solution mixture into a thin sheet of relatively large surface area so that volatile component(s) therein can be more easily released, by chemical reaction mediated generation, into a gaseous phase in the form of sequentially varying numbers of quantized bubbles, which sequentially varying numbers of quantized bubbles are caused to merge in the elevated internal pressure supporting gas/liquid separator chamber by elevated pressure therein, to provide said relatively sequentially constant buffered pressure and flow rate of gaseous phase volatile component(s) sample out of said gaseous phase volatile component(s) sample outlet port, which generating and providing system further comprises a carrier gas inlet port in said elevated internal pressure supporting gas/liquid separator chamber, into which carrier gas is caused to flow during use to aid the flow of generated gaseous phase volatile component(s) sample through said gaseous phase volatile component(s) sample outlet port and into a sample analysis system attached thereto, which entered carrier gas is oriented to flow through said elevated internal pressure supporting gas/liquid separator chamber in a tangentially oriented spiral manner toward said gaseous phase volatile components sample outlet port, which elevated internal pressure supporting gas/liquid separator chamber is tapered in shape toward said gaseous phase volatile components sample outlet port.

6. A system for generating and providing a gaseous phase volatile component(s) sample to a sample analysis system at relatively sequentially constant buffered pressure and flow rate, via a gaseous phase volatile component(s) sample outlet port in a gas/liquid separator chamber, which volatile component(s) are originally present in a liquid solution mixture having entered by way of a liquid sample entry means, which generating and providing system includes a drain outlet in said gas/liquid separator chamber, to which during use, is attached a sealed pump system for use in quickly, immediately and actively removing remaining liquid solution mixture having entered thereto during use, after volatile component(s) have been generated therefrom by a chemical reaction mediated process, which system for generating and providing a gaseous phase volatile component(s) sample to a sample analysis system at a relatively constant buffered pressure and flow rate, comprises an elevated internal pressure supporting gas/liquid separator chamber which is tapered in shape toward said gaseous phase volatile component(s) sample outlet port, so as to enhance tangentially directed carrier gas aided volatile component(s) containing gaseous phase sample transport therethrough during use, said volatile component(s) containing gaseous phase sample transport enhancing tangentially directed carrier gas flow having entered by way of a carrier gas inlet port present, in said elevated internal pressure supporting gas/liquid separator chamber, at an extent thereof laterally opposed to the location of said gaseous phase volatile component(s) sample outlet port.

7. A system for generating and providing a gaseous phase component(s) sample to a sample analysis system at essentially constant pressure and flow rate comprising:

a. mixing elements;
   b. a length of enclosed volume flow path;
   c. an elevated internal pressure supporting gas/liquid separator chamber comprising:
      1. a liquid sample entry means;
      2. a surface area providing means;
      3. a carrier gas inlet port;
      4. a gaseous phase volatile component(s) outlet port; and
      5. a drain outlet; and
   d. a sealed pump system;

which mixing elements serve to mix chemicals with a volatile component(s) containing liquid sample to form a volatile component(s) containing liquid sample mixture such that volatile component(s) releasing chemical reactions occur therein, which chemically reacting volatile component(s) in said volatile component(s) containing liquid sample mixture are caused to flow through said length of enclosed volume flow path and enter said elevated internal pressure supporting gas/liquid separator chamber via said liquid sample entry means, and impinge upon said surface area providing means therein which is positioned offset from said liquid sample entry means, such that said volatile component(s) containing solution mixture is caused to flow over said surface area providing means and form a relatively large surface area thin sheet from which chemically reacting gaseous phase volatile component(s) are easily and efficiently released in sequentially varying numbers of quantized bubbles, which released volatile gaseous phase component(s) are aided in transport through said gaseous phase volatile component(s) outlet port by the entry of a carrier gas at said carrier gas inlet port present at an extent of said elevated internal pressure supporting gas/liquid separator chamber opposed to the location of said liquid sample entry means, which gaseous phase volatile component(s) outlet port comprises a length of small internal diameter tubing which serves to maintain the pressure inside said elevated internal pressure supporting gas/liquid separator chamber while allowing said gaseous phase volatile component(s) containing sample to flow therethrough; which drain outlet in said elevated internal pressure supporting gas/liquid separator chamber is positioned below said surface area providing means such that volatile component(s) containing liquid sample mixture which impinges upon said surface area providing means flows off said surface area providing means and falls into said drain outlet, attached to which drain outlet is a sealed pump system which serves to quickly, immediately and actively remove said volatile component(s) containing liquid sample mixture, after release of volatile gaseous component(s) therefrom, in a manner that maintains internal pressure inside said elevated internal pressure supporting gas/liquid separator chamber above that outside thereof, and which elevated internal pressure supporting gas/liquid separator chamber is tapered in shape, narrowing toward said gaseous phase volatile component(s) outlet port such that carrier gas having entered said carrier gas inlet port causes a tangentially oriented spiral flow of gaseous phase volatile component(s) released from said volatile component(s) containing liquid sample mixture toward said gaseous phase volatile component(s) outlet port, the maintaining of said elevated pressure inside said elevated pressure supporting gas/liquid separator chamber being performed to provide a buffered relatively constant sequential pressure and flow rate of gaseous phase volatile component(s) sample out of said gaseous phase volatile component(s) outlet port by effecting an individual quantized bubble effect diminishing merging of said sequentially varying numbers of chemical reaction released gaseous phase sample component(s) containing quantized bubbles.

* * * * *